United States Patent [19]

Pickett

[11] Patent Number: 5,391,795
[45] Date of Patent: Feb. 21, 1995

[54] SILYLATED AGENTS USEFUL FOR ABSORBING ULTRAVIOLET LIGHT

[75] Inventor: James E. Pickett, Schenectady, N.Y.

[73] Assignee: General Electric Company, Schenectady, N.Y.

[21] Appl. No.: 198,753

[22] Filed: Feb. 18, 1994

[51] Int. Cl.[6] .................................. C07F 7/08
[52] U.S. Cl. ................... 556/436; 106/287.14; 428/412; 428/447
[58] Field of Search ............... 556/436; 106/287.14; 428/412, 447

[56] References Cited

U.S. PATENT DOCUMENTS

| | | |
|---|---|---|
| 4,278,804 | 7/1981 | Ashby et al. . |
| 4,322,455 | 3/1982 | Olson et al. . |
| 4,373,061 | 2/1983 | Ching . |
| 4,467,082 | 8/1984 | Shirahata et al. ............... 556/436 X |
| 5,210,247 | 5/1993 | Haberle et al. ................ 556/436 X |
| 5,214,085 | 3/1993 | Patel et al. . |

*Primary Examiner*—Paul F. Shaver
*Attorney, Agent, or Firm*—Edward A. Squillante, Jr.; William H. Pittman

[57] ABSTRACT

Novel silylated agents capable of absorbing ultraviolet light are incorporated into silicone hardcoats and used to coat polycarbonate substrates. The coated polycarbonate substrates display improved resistances to abrasion and ultraviolet light.

17 Claims, No Drawings

SILYLATED AGENTS USEFUL FOR ABSORBING ULTRAVIOLET LIGHT

FIELD OF THE INVENTION

This invention relates to novel silylated agents capable of absorbing ultraviolet light. More particularly, the silylated agents are 4,6-dibenzoyl-2-(trialkoxysilylalkyl) resorcinols which are photostable and compatible in silicone hardcoat matrices.

BACKGROUND OF THE INVENTION

Thermoplastic resins are characterized by their many advantageous properties which include optical clarity, high ductility, high heat deflection temperature as well as dimensional stability. As a result of such properties, they are often employed in many commercial applications.

While thermoplastic resins possess the above-described advantageous properties, they often display low abrasion and chemical solvent resistances, and like many other organic polymeric materials, they are susceptible to photodegradation by ultraviolet light. The photodegradation typically results in unfavorable characteristics including yellowing and erosion of the polymer surface.

It is of increasing interest to prepare thermoplastic resins; particularly polycarbonates, that are resistant to abrasion and photodegradation. Such preparation conventionally employs treating the polycarbonate surface with a coating material (silicone hardcoat matrix), whereby the coating material typically contains ultraviolet light absorbing agents such as benzophenone and benzotriazole derivatives.

It is often discovered, however, that the ultraviolet light absorbing agents, themselves, decompose upon exposure to ultraviolet light. This invariably causes microcracks to form in the coating material and leads to a degradation of the favorable properties of the polycarbonate which the agents are originally employed to protect.

The instant invention, therefore, is directed to novel silylated agents capable of absorbing ultraviolet light. Said silylated agents are 4,6-dibenzoyl-2-(trialkoxysilylalkyl) resorcinols which display improved photostability as well as compatibility in silicone hardcoat matrices.

DESCRIPTION OF THE PRIOR ART

Efforts have been disclosed for preparing coated plastic substrates. In commonly assigned U.S. Pat. No. 4,278,804, plastics are coated with a composition comprising silanol-reactive alkoxysilyl- or alkanoyloxysilylalkyl ether adducts of aromatic ultraviolet absorbing agents.

Additionally, in commonly assigned U.S. Pat. No. 4,373,061, thermoplastic substrates coated with a silicone hardcoat composition comprising benzophenones as ultraviolet absorbing compounds are disclosed.

Still other investigators have focused on coating compositions for plastics. In commonly assigned U.S. Pat. No. 5,214,085, coating compositions comprising benzophenones or benzotriazoles as ultraviolet absorbing agents are disclosed.

The instantly claimed invention is patentably distinguishable from the above-described since, among other reasons, it is directed to novel silylated agents capable of absorbing ultraviolet light. The silylated agents are 4,6-dibenzoyl-2-(trialkoxysilylalkyl) resorcinols which display improved photostability as well as compatibility in silicone hardcoat matrices. Moreover, improved photostability is defined as a rate of photodegradation exhibiting a loss of less than about 0.75 and preferably less than about 0.1 and most preferably less than about 0.05 absorbance units/1000 hr xenon arc as described in Pickett et al., Polymer Degradation and Stability, 42, 231 (1993).

SUMMARY OF THE INVENTION

In a first aspect, the instant invention is directed to novel silylated agents having improved photostabilities and capable of absorbing ultraviolet light. The silylated agents are 4,6-dibenzoyl-2-(trialkoxysilylalkyl) resorcinols having the formula

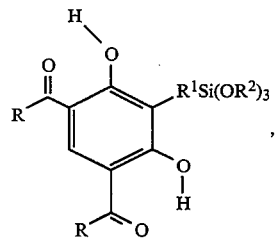

wherein each R is independently a substituted or unsubstituted monocyclic or polycyclic aromatic radical, $R^1$ is carbon or a linear or branched aliphatic chain having less than about 10 carbons and $R^2$ is a $C_{1-6}$ alkyl group. Often, however, the silylated agent is a 4,6-dibenzoyl-2-(3-trialkoxysilylalkyl) resorcinol and preferably 4,6-dibenzoyl-2-(3-triethoxysilylpropyl) resorcinol.

In a second aspect of the instant invention, the novel silylated agents described above are incorporated into thermally cured silicon compound-containing compositions. Said compositions comprising the silylated agents are coating compositions defined as silicone hardcoats or topcoats.

In a third aspect of the instant invention, the above-described silicone hardcoats or topcoats are applied to the surface of a solid substrate thus producing a coated solid substrate having improved resistances to abrasion and especially ultraviolet light. Such coated solid substrates are often referred to as weatherable substrates. Further, there are no limitations with respect to the thickness of the silicone hardcoats applied to said solid substrates. They are, however, often about 0.5 to about 50 μm thick and preferably about 3 to about 10 μm thick. In the instant invention, the solid substrates that may be employed often include polymer substrates such as acrylic polymers including poly(methyl methacrylate), polyesters such as poly(ethylene terephthalate) and poly(butylene terephthalate), polyamides, polyimides, acrylonitrile-styrene copolymers, styrene-acrylonitrile-butadiene copolymers, polyvinyl chloride, polystyrene, blends of polystyrene and polyphenylene ethers, butyrates, polyethylene and the like. Moreover, said solid substrates may also include metal substrates, painted surfaces, glass, ceramics and textiles.

However, the coating compositions of the instant invention are preferably employed to coat polycarbonates.

DETAILED DESCRIPTION OF THE PREFERRED EMBODIMENTS

Preparation of the 4,6-dibenzoyl-2-(trialkoxysilylalkyl) resorcinols employed in the instant invention is achieved, for instance, by first mixing a benzoyl halide and an aluminum halide in an organic solvent with a dialkoxybenzene to produce a 4,6-dibenzoylresorcinol. The 4,6-dibenzoylresorcinol is subsequently subjected to a quaternary ammonium salt and an allyl halide under basic conditions to produce a 2-allyl-4,6-dibenzoylresorcinol. The 2-allyl-4,6-dibenzoylresorcinol is contacted with a trialkoxysilane in the presence of a hydrosilylation catalyst in order to produce the desired 4,6-dibenzoyl-2-(trialkoxysilylalkyl) resorcinol.

The preparation of the silylated agents of the instant invention is further illustrated by the following examples. Molecular structures of all products in the examples may be confirmed by proton and carbon-13 nuclear magnetic resonance spectroscopy.

EXAMPLE 1

A 500 mL 3-necked flask fitted with a gas scrubber, thermometer and magnetic stirrer was charged with 28.1 g (200 mmol) of benzoyl chloride and 100 mL of methylene chloride to produce a solution. The solution was cooled to 5° C. and 27.0 g (203 mmol) of anhydrous aluminum chloride were added in two portions keeping the temperature below 20° C. The resulting mixture was cooled to 5° C. 13.8 g (100 mmol) of 1,3-dimethoxybenzene were added dropwise over the course of about 30 minutes and the temperature was kept below 10° C. The mixture was stirred for about 1 hour at room temperature and subsequently heated to reflux. After heating overnight, the mixture was cooled and 20 mL of concentrated HCl were added dropwise. 100 mL of water and 50 mL of methylene chloride were then added and the resulting aqueous and organic phases were separated. The organic phase was evaporated to dryness and the resulting solid was recrystallized two times from a boiling ethanol/toluene mixture. 16.21 g (51%) of 4,6-dibenzoylresorcinol were recovered.

EXAMPLE 2

A round bottomed flask equipped with a reflux condenser and magnetic stirrer was charged with 6.36 g (20 mmol) of 4,6-dibenzoylresorcinol, as prepared in Example 1, and 22 ml of 1.0N aqueous NaOH. 63 mg of tetrabutylammonium bromide and 10.0 ml of allyl chloride were added to produce a reaction mixture. The reaction mixture was stirred vigorously and heated at reflux for about 5 hours. Excess allyl chloride was distilled and recovered and 1 ml of 5% aqueous HCl was added to neutralize any excess base. The resulting solid was filtered and recrystallized from an ethanol/chloroform mixture to yield 4.8 g (67%) of 2-allyl-4,6-dibenzoylresorcinol.

EXAMPLE 3

5.0 g (14 mmol) of 2-allyl-4,6-dibenzoylresorcinol, as prepared in Example 2, were dissolved in 20 ml of warm toluene. One drop of Karstedt's catalyst (complex of 1,3-divinyl-tetramethyidisiloxane with platinum) was added to produce a mixture. The mixture was heated to 80° C. and 5 ml of triethoxysilane were added. Heating continued for about 1 hour and the mixture was cooled to room temperature. A precipitate formed and was removed by filtration. The filtrate was filtered through silica gel which was washed with chloroform and evaporated under reduced pressure. 7.04 g (96%) of 4,6-dibenzoyl-2-(3-triethoxysilylpropyl) resorcinol were recovered. Ultraviolet spectrum indicated (CHCl$_3$): $\lambda_{max}$ 289 nm ($\epsilon$=33,200), 330 nm (shoulder, $\epsilon$=6,800).

EXAMPLE 4

Example 4 was prepared in a manner similar to Example 1 except that 15.4 g (100 mmol) of meta-toluyl chloride was used in lieu of benzoyl chloride and subsequent to the addition of the 1,3-dimethoxybenzene, 14.0 g (100 mmol) of benzoyl chloride and 13.3 g of AlCl$_3$ were added. Recovered were 8.45 g (25% yield) of 4-(3'-methylbenzoyl)-6-benzoyl resorcinol.

EXAMPLE 5

Example 5 was prepared in a manner similar to Example 2 except that 3.32 g (10 mmol) of 4-(3'-methylbenzoyl)-6-benzoylresorcinol was used in lieu of 4,6-dibenzoylresorcinol. 1.94 g (52%) 3-allyl-4-(3'-methylbenzoyl)-6-benzoylresorcinol was recovered and treated with triethoxysilane as described in Example 3. Recovered were 2.39 g (95%) silylated methyl dibenzoylresorcinol. This substituted product may also be added to the silicon compositions described in the invention to produce a silicone hardcoat.

EXAMPLE 6

Example 6 was prepared in a manner similar to Example 2 except that 3-chloro-2-methyl-1-propene was used in lieu of allyl chloride and work-up proceeded as in Example 2 producing 1.80 g (48%) C-alkylated solid product. The C-alkylated solid product was treated with triethoxysilane as described in said Example 3 except that the reaction mixture was heated overnight with 3 drops of catalyst. Recovered were 1.96 g (92%) of 2-(2-methyl-3-triethoxysilylpropyl)-4,6-dibenzoylresorcinol.

The novel silylated agents described above may be incorporated into thermally cured silicon compound-containing compositions to produce a silicone hardcoat. There are no limitations with respect to the type of silicon compound-containing compositions that may be employed in the instant invention other than that they are compatible with the novel silylated agents described above. Hence, for example, the compositions can be acidic, basic or neutral in nature, and the only requirement for said silicone compound-containing compositions is that they are miscible with the novel silylated agents of the instant invention.

Examples of the silicon compound-containing compositions that may be employed in this invention are those prepared by hydrolyzing in an aqueous dispersion of colloidal silica and a trialkoxysilane or mixtures of trialkoxysilanes having the formula $$RSi(OR)_3, \qquad \text{II}$$

wherein each R is independently an alkyl group having 1 to 3 carbon atoms or a substituted or unsubstituted aromatic radical; preferably, a methyl group.

To said silicon compound-containing compositions are added the silylated agents of the instant invention to produce a silicone hardcoat or topcoat liquid resin. The liquid resin subsequent to curing is defined as a silicone hardcoat or topcoat.

It is also within the scope of the instant invention to include conventional additives such as polysiloxane polyether copolymers and the like in the silicon hardcoat resin since such additives have been found to reduce the incidence of stress cracking in the hardcoat. Other additives including thickening agents, pigments, dyes and the like may also be included for their conventionally employed purposes.

A detailed description for the preparation of silicon compound-containing compositions as well as silicone hardcoats may be found in commonly assigned U.S. Pat. No. 4,373,061, the disclosure of which is incorporated by reference.

Moreover, in lieu of or in conjunction with the above-described silicone hardcoats, it is within the scope of the instant invention to employ ultraviolet radiation stabilizing compositions which consist essentially of the novel silylated agents of the instant invention and at least one liquid carrier which is nonaggressive towards the polycarbonate. The liquid carrier is selected from the class consisting of alcohols, hydroxy ethers, alcohol-water mixtures, liquid aliphatic hydrocarbons, liquid cycloaliphatic hydrocarbons, and chlorofluorocarbons. When employing such compositions, the polycarbonates are preheated, before being contacted with the composition, to a temperature sufficient for the silylated agents to effectively impregnate the surface layers of said polycarbonate. The process for preparing and treating polycarbonates with such compositions is described in commonly assigned U.S. Pat. No. 4,322,455, the disclosure of which is incorporated herein by reference.

The following additional examples are to further illustrate and facilitate the production of the silicone hardcoats of the instant invention.

EXAMPLE 7

0.5 g of 4,6-dibenzoyl-2-(3-triethoxysilylpropyl) resorcinol as prepared in Example 3 was added to 50 g of silica resin (condensed methyl trimethoxy silane/aqueous colloidal silica resin at approximately 20% solids in an alcohol solvent) to produce a mixture. The mixture was stirred overnight and passed through a 0.30 micron filter yielding a silicone hardcoat solution with 5 pph silylated ultraviolet absorbing agent based on solids. The solution was applied to a glass slide. Subsequent to solvent evaporation and baking at 100° C. for 1 hour, an optically clear silicone hardcoat was formed on the glass.

EXAMPLE 8

Example 8 was prepared in a manner similar to Example 7 except that 0.2 g of 4,6-dibenzoyl-2-(3-triethoxysilylpropyl) resorcinol was added to 10 g of silica resin to produce a solution with 10 pph silylated ultraviolet absorbing agent based on solids. After filtering and aging the solution, it was flow coated onto a glass slide and baked to yield an optically clear silicone hardcoat on the slide.

The polycarbonate compositions employed in the instant invention may comprise structural units of the formulae

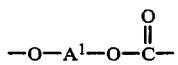

and

-continued

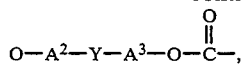

wherein IV is a preferred subgenus of III and $A^1$ is a divalent substituted or unsubstituted aliphatic, alicyclic or aromatic radical, preferably —$A^2$—Y—$A^3$— wherein $A^2$ and $A^3$ are each independently a monocyclic divalent aromatic radical. Y is a bridging radical in which 1 to 4 atoms separate $A^2$ from $A^3$ and IV is a preferred subgenus of III.

The $A^2$ and $A^3$ values may be unsubstituted phenylene or substituted derivatives thereof, illustrative substituents (one or more) being alkyl; alkenyl, alkoxy and the like. Unsubstituted phenylene radicals are preferred. Both $A^2$ and $A^3$ are preferably p-phenylene, although both may be o- or m-phenylene or one o- or m-phenylene and the other p-phenylene.

The bridging radical, Y, is one in which one or two atoms, preferably one, separate $A^2$ from $A^3$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gemalkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred units of formula IV are 2,2-bis(4-phenylene)propane carbonate units, which are derived from bisphenol A and in which Y is isopropylidene and $A^2$ and $A^3$ are each p-phenylene.

The material represented by formula V

is the source of structural units of formula III above; $A^1$ is as previously defined.

Illustrative non-limiting examples of V include: 2,2-bis(4-hydroxyphenyl)-propane (bisphenol A); 2,2-bis(3,5-dibromo-4-hydroxyphenyl)propane; 2,2-bis(3,5-dimethyl-4-hydroxyphenyl)propane; 1,1-bis(4-hydroxyphenyl)cyclohexane; 1,1-bis(3,5-dimethyl-4-hydroxyphenyl)cyclohexane; 1,1-bis(4-hydroxyphenyl)decane; 1,4-bis(4-hydroxyphenyl)propane; 1,1-bis(4-hydroxyphenyl)cyclododecane; 1,1-bis(3,5-dimethyl-4-hydroxyphenyl)cyclododecane; 4,4-dihydroxydiphenyl ether; 4,4-thiodiphenol; 4,4-dihydroxy-3,3-dichlorodiphenyl ether; 4,4-dihydroxy-3,3-dihydroxydiphenyl ether; 1,3 benzenediol; and 1,4-benzenediol.

Other useful dihydroxyaromatic compounds which are also suitable for use in the preparation of the above copolycarbonates are disclosed in U.S. Pat. Nos. 2,999,835; 3,028,365; 3,334,154 and 4,131,575, all of which are incorporated herein by reference. The preferred bisphenol is 2,2-bis(4-hydroxyphenyl)propane (bisphenol A).

The polycarbonates (homopolycarbonates or copolycarbonates) employed in the instant invention may be prepared by reacting bisphenols with a carbonate source such as phosgene or dimethyl carbonate using conventional techniques. These include melt polymerization, interfacial polymerization and interfacial conversion with bischloroformate followed by polymerization. Chain termination agents such as phenol may also be employed.

The silicone hardcoats described above may be applied to solid substrates such as polycarbonates by conventional techniques which include dipping, brushing, roller coating or flow coating.

Following application, the silicone hardcoats are cured by exposure to heat. They often cure at temperatures from about 90° to about 130° C. without the aid of a curing catalyst. If milder curing conditions are desired, it is within the scope of the instant invention to employ curing catalysts such as sodium acetate, potassium formate, ammonium carboxylates as well as those disclosed in commonly assigned U.S. Pat. No. 4,278,804, the disclosure of which is incorporated herein by reference.

Primer compositions typically employed when coating solid substrates with silicone hardcoats may also be employed in the instant invention. Such compositions typically comprise thermoplastic acrylic polymers and organic solvents. It is also within the scope of the instant invention to employ, as primers, emulsions of thermosettable acrylic polymers and water as well as acrylic polymer compositions in emulsions; additionally, it is within the scope of the instant invention to include ultraviolet light absorbing agents in the above-described primers. Further, there are no limitations with respect to the thickness of the primers applied; however, they are often about 0.01 to about 50 $\mu$m thick and preferably about 0.1 to about 10 $\mu$m thick. A detailed description for the preparation and application of the above-referenced primers may be found in commonly assigned U.S. Pat. No. 4,410,594, the disclosure of which is incorporated herein by reference. Moreover, it is often preferred that the thermoplastic acrylic polymer employed is poly(methylmethacrylate).

Example 9 illustrates the coating of a preferred polycarbonate.

EXAMPLE 9

A polycarbonate sample (BPA) primed with polymethylmethacrylate (1.0 $\mu$m) was flow coated with a silicone hardcoat solution as prepared in Example 7. The coated sample was baked for 90 minutes at 100° C. yielding a polycarbonate with an optically clear 5.0 $\mu$m silicone hardcoat. The coating was subjected to a Taber abrasion test (ASTM D1044, CS-10F wheels, 500 cycles) and exhibited a change of haze of 11.9% indicating favorable resistance to abrasion.

The data in the table which follows has been compiled to demonstrate that the novel silylated agents of the instant invention unexpectedly possess superior photostabilities and microcracking properties.

The following structures correspond to the entries in the table hereinbelow. Entries 1–6 are based on ultraviolet light absorbing agents commonly employed in the art. Entry 7 is the preferred novel silylated ultraviolet light absorbing agent of the instant invention as depicted by formula I. It is most preferred that the rate of photodegradation is as slow as possible.

-continued

| Entry | |
|---|---|
| 5 | 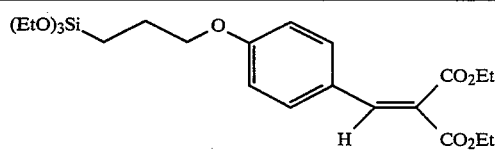 |
| 6 | 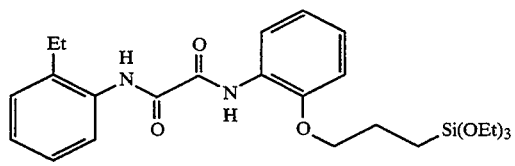 |
| 7 | 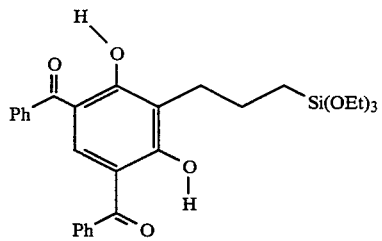 |

TABLE

| Entry | Rate of Photodegradation[A] Absorbance/1000 hr xenon arc | Time to Onset of Cracking (hours)[C] |
|---|---|---|
| 1 | 0.20 | 1,500 |
| 2 | 0.84 | <2,000 |
| 3 | 0.74 | <2,000 |
| 4 | 2.06 | " |
| 5 | 4.8 | " |
| 6 | 0.84 | " |
| 7 | 0.04 | 6,500 |
| 8[B] | — | >8,000 |

[A]The ultraviolet light absorbing agents (Entries 1–7) were formulated into 7 silicone hardcoat resins comprising an ammoniun-stabilized colloidal silica of pH 3.1 at 12% on solids. Glass slides were flow coated with the hardcoat resins and baked at 130° C. for 60 minutes to produce a hardcoat. The slides were then exposed to an Atlas Ci35a xenon arc weatherometer in order to obtain the rates of photodegradation.
[B]Entry 8 is the silicone hardcoat control without an ultraviolet light absorbing agent.
[C]Glass slides coated with the above silicone hardcoats and exposed to an Atlas Ci35a xenon arc weatherometer to determine the onset of microcracking.

What is claimed is:

1. A silylated agent useful for absorbing ultraviolet light having the formula

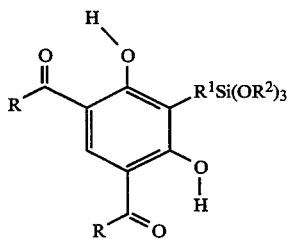

wherein each R is independently a substituted or unsubstituted monocyclic or polycyclic aromatic radical and $R^1$ is carbon or a linear or branched aliphatic chain having less than about 10 carbons and $R^2$ is a $C_{1-6}$ alkyl group.

2. A silylated agent useful for absorbing ultraviolet light in accordance with claim 1 wherein said silylated agent is 4,6-dibenzoyl-2-(3-triethoxysilylpropyl) resorcinol.

3. A silicone hardcoat comprising:
(a) a silylated agent having the formula

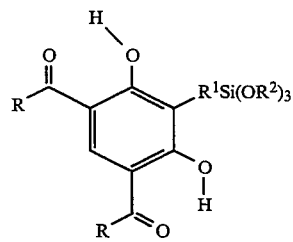

wherein each R is independently a substituted or unsubstituted monocyclic or polycyclic aromatic radical and $R^1$ is carbon or a linear or branched aliphatic chain having less than about 10 carbons and $R^2$ is a $C_{1-6}$ alkyl group; and
(b) a silicon compound containing composition.

4. A silicone hardcoat in accordance with claim 3 wherein said silicon compound containing composition has the formula $$RSi(OR)_3,$$

wherein each R is independently an alkyl group having 1 to 3 carbon atoms or a substituted or unsubstituted aromatic radical.

5. A silicone hardcoat in accordance with claim 4 wherein each R is a methyl group.

6. A silicone hardcoat in accordance with claim 3 wherein said silylated agent useful for absorbing ultraviolet light is 4,6-dibenzoyl-2-(3-triethoxysilylpropyl) resorcinol.

7. A solid substrate with a silicone hardcoat applied thereon wherein said silicone hardcoat comprises:
(a) a silylated agent useful for absorbing ultraviolet light having the formula

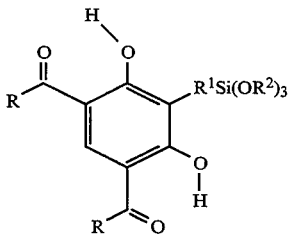

wherein each R is independently a substituted or unsubstituted monocyclic or polycyclic aromatic radical and $R^1$ is carbon or a linear or branched aliphatic chain having less than about 10 carbons and $R^2$ is a $C_{1-6}$ alkyl group; and (b) a silicon compound containing composition.

8. A solid substrate in accordance with claim 7 wherein said silicon compound containing composition has the formula

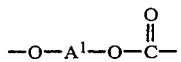

wherein each R is independently an alkyl group having 1 to 3 carbon atoms or a substituted or unsubstituted aromatic radical.

9. A solid substrate in accordance with claim 8 wherein each R is a methyl group.

10. A solid substrate in accordance with claim 7 wherein said silylated agent useful for absorbing ultraviolet light is 4,6-dibenzoyl-2-(3-triethoxysilylpropyl) resorcinol.

11. A solid substrate in accordance with claim 7 wherein said solid substrate is a polycarbonate.

12. A solid substrate in accordance with claim 11 wherein said polycarbonate is a homopolycarbonate.

13. A solid substrate in accordance with claim 11 wherein said polycarbonate is a copolycarbonate.

14. A solid substrate in accordance with claim 11 wherein said polycarbonate comprises structural units of the formula $$-O-A^1-O-\overset{O}{\underset{\|}{C}}-$$

and $A^1$ is a divalent substituted or unsubstituted aliphatic, alicyclic or aromatic radical.

15. A solid substrate in accordance with claim 14 wherein $A^1$ is $A^2-Y-A^3$ and $A^2$ and $A^3$ are each independently a macrocyclic divalent aromatic radical and Y is a bridging radical.

16. A solid substrate in accordance with claim 15 wherein said polycarbonate is bisphenol A polycarbonate.

17. A solid substrate in accordance with claim 7 wherein said solid substrate is treated with a primer prior to applying said silicone hardcoat.

* * * * *